United States Patent
Antler

(10) Patent No.: US 6,453,912 B1
(45) Date of Patent: Sep. 24, 2002

(54) DENTAL FLOSS WITH ABRASIVES

(76) Inventor: Steven M. Antler, 6 Shields La., Darien, CT (US) 06820

( * ) Notice: Subject to any disclaimer, the term of this patent is extended or adjusted under 35 U.S.C. 154(b) by 0 days.

(21) Appl. No.: 09/977,489

(22) Filed: Oct. 16, 2001

Related U.S. Application Data

(60) Provisional application No. 60/266,483, filed on Feb. 6, 2001, and provisional application No. 60/251,569, filed on Dec. 7, 2000.

(51) Int. Cl.[7] ................................................. A61C 15/00
(52) U.S. Cl. ........................................................ 132/321
(58) Field of Search ................................. 132/321, 322, 132/323, 324, 326, 327, 328, 329; 424/50

(56) References Cited

U.S. PATENT DOCUMENTS

| | | |
|---|---|---|
| 431,713 A | 7/1890 | Whaley |
| 579,139 A | 3/1897 | Deardorff |
| 1,969,874 A | 8/1934 | Butterfield |
| 2,122,920 A | 7/1938 | Russell |
| 2,328,998 A | 9/1943 | Radford |
| 2,623,003 A | 12/1952 | Friedlob et al. |
| 3,605,347 A | 9/1971 | Barry |
| 3,613,143 A | 10/1971 | Muhler et al. |
| 3,699,979 A | 10/1972 | Muhler et al. |
| 3,838,702 A | 10/1974 | Standish et al. |
| 4,222,143 A | 9/1980 | Tarrson et al. |
| 4,373,541 A | 2/1983 | Nishioka |
| 4,509,875 A | 4/1985 | Shintani |
| 4,986,288 A | * 1/1991 | Kent et al. ................. 132/321 |
| 5,033,488 A | 7/1991 | Curtis et al. |
| 5,071,348 A | 12/1991 | Woog |
| 5,117,848 A | 6/1992 | Huang |
| 5,118,291 A | 6/1992 | Varaine |
| 5,159,943 A | 11/1992 | Richards et al. |
| 5,161,971 A | 11/1992 | Neiner et al. |
| 5,226,929 A | 7/1993 | Morii et al. |
| 5,283,924 A | 2/1994 | Kaminsky et al. |
| 5,377,703 A | 1/1995 | Chou et al. |
| 5,386,278 A | 1/1995 | Maeyama et al. |
| 5,611,687 A | 3/1997 | Wagner |
| 5,678,275 A | 10/1997 | Derfner |
| 5,699,578 A | 12/1997 | Dumler et al. |
| 5,722,106 A | 3/1998 | Masterman et al. |
| 5,735,011 A | 4/1998 | Asher |
| 5,851,116 A | 12/1998 | Margolis |
| 5,903,951 A | 5/1999 | Ionta et al. |
| 5,967,154 A | 10/1999 | Anderson |
| 5,974,619 A | 11/1999 | Weihrauch |
| 5,975,901 A | 11/1999 | Kennedy |
| 6,082,999 A | 7/2000 | Tcherny et al. |

* cited by examiner

Primary Examiner—Todd E. Manahan
(74) Attorney, Agent, or Firm—Shlesinger, Arkwright & Garvey LLP

(57) ABSTRACT

A dental floss comprises a plurality of polyamide monofilaments joined together; and a plurality of abrasive particles integrated into each monofilament.

15 Claims, 1 Drawing Sheet

DENTAL FLOSS WITH ABRASIVES

RELATED APPLICATIONS

This is a nonprovisional application claiming the priority benefits of application Ser. Nos. 60/266,483, filed on Feb. 6, 2001, and Ser. No. 60/251,569, filed on Dec. 7, 2000, all of which are hereby incorporated by reference.

FIELD OF THE INVENTION

The present invention is directed to a dental floss containing abrasive particles for removing plaque, tooth stain and food debris between teeth.

OBJECTS AND SUMMARY OF THE INVENTION

It is an object of the present invention to provide a dental floss containing abrasive particles for removing plaque, tooth stain and food debris between teeth.

In summary, the present invention is directed to a dental floss comprising a plurality of polyamide monofilaments joined together to form a strand; and a plurality of abrasive particles integrated into each monofilament.

The present invention also provides a method for making dental floss, comprising:
  a) mixing a polyamide resin with abrasive particles wherein the particles comprise about 2%–10% by weight of the mixture;
  b) extruding the mixture to form a filament of about 0.002"–0.004" in diameter; and
  c) joining a plurality of the filaments to form the dental floss.

This and other objects of the present invention will become apparent from the following detailed description.

DETAILED DESCRIPTION OF THE INVENTION

Figure 1:
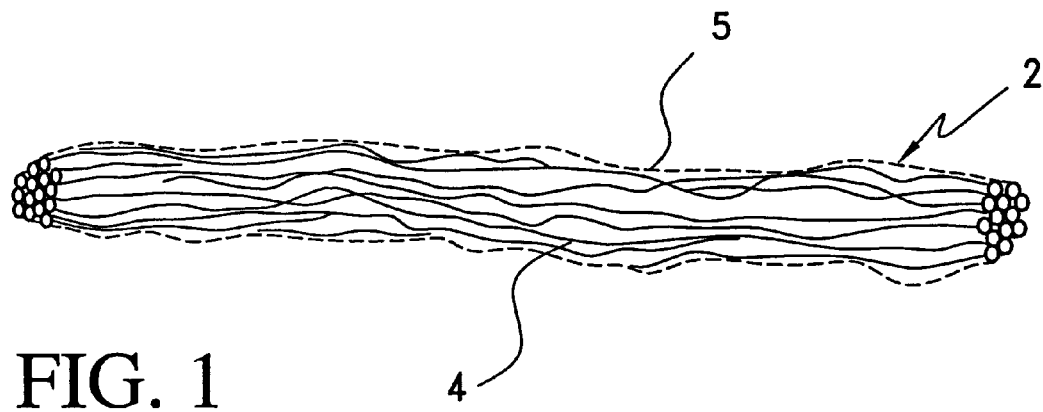
FIG. 1 is a schematic perspective view of a dental floss made in accordance with the present invention.
Figure 2:
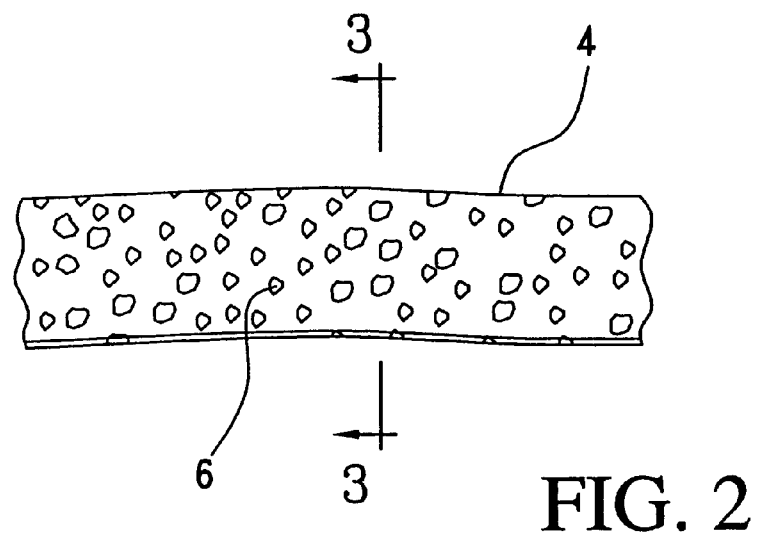
FIG. 2 is an enlarged schematic side elevational view of a monofilament used to make the dental floss of FIG. 1.
Figure 3:
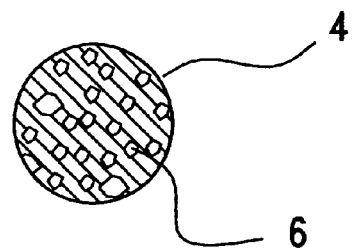
FIG. 3 is a cross-sectional view taken along line 3—3 of FIG. 2.

A dental floss made in accordance with the present invention for removing tooth stain is disclosed in FIG. 1. The dental floss 2 is made from a plurality of monofilaments 4 joined together by conventional means to form a strand 5 of much larger cross-sectional area. The monofilaments 4 are preferably made of nylon, and includes abrasive particles 6 integrated into the monofilament, as best shown in FIGS. 2 and 3. The abrasive particles 6 are preferably made of aluminum oxide; however, other abrasive or polishing particles may be used. White aluminum oxide is a type of abrasive well known in the abrasive industry. The abrasive particles are advantageously integrated into the filament during manufacture of the filament by mixing the resin with the particles prior to the extrusion process. The dental floss 2 may be round or flat in cross-section.

As an example, Nylon 612 resin is mixed with aluminum oxide particles with average particle size of 10 microns, with a range of 4–27 microns. The abrasive particles preferably make up about 2%–10% by weight of the total mixture. The mixture is then extruded in a conventional way to form a monofilament, 0.002"–0.004" in diameter. It should be understood that some of the abrasive particles will be disposed near the surface of the monofilament after extrusion and, thereby be exposed, as generally depicted in FIG. 2. A plurality of the monofilaments, approximately 50–500 fibers, are joined together in a conventional way, such as by weaving, pleating or twisting, to make a strand of dental floss. Nylon 612, available from DuPont, is a polyamide with desirable characteristics for use in making industrial brushes, paint brushes, etc.

The dental floss is sized to be inserted between the teeth. The abrasive particles are preferably sized and added in the preferred weight ratios to effectively remove plaque and food particles from the surfaces of teeth while maintaining the high tensile strength of the filament.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

I claim:

1. A dental floss, comprising:
  a) a plurality of polyamide monofilament joined together to form a strand; and
  b) a plurality of abrasive particles integrated into each monofilament.

2. A dental floss as in claim 1, wherein said abrasive particles include aluminum oxide.

3. A dental floss as in claim 1, wherein said abrasive particles include white aluminum oxide.

4. A dental floss as in claim 3, wherein said abrasive particles have sizes of about 4–27 microns.

5. A dental floss as in claim 1, wherein said abrasive particles have average particle size of about 10 microns.

6. A dental floss as in claim 1, wherein said abrasive particles are about 2%–10% by weight.

7. A dental floss as in claim 1, wherein said monofilament is about 0.002"–0.004" in diameter.

8. A dental floss as in claim 1, wherein said monofilament is Nylon 612.

9. A dental floss, comprising:
  a) a plurality of nylon monofilaments joined together to form a strand;
  b) a plurality of abrasive particles integrated into each monofilament during manufacture of said monofilament;
  c) said abrasive particles comprise about 2%–10% by weight of each monofilament; and
  d) said monofilament is about 0.002"–0.004" in diameter.

10. A dental floss as in claim 9, wherein said monofilament is Nylon 612.

11. A dental floss as in claim 9, wherein particles have an average size of about 10 microns.

12. A method for making dental floss, comprising:
  a) mixing a polyamide resin with abrasive particles wherein the particles comprise about 2%–10% by weight of the mixture;
  b) extruding the mixture to form a monofilament of about 0.002"–0.004" in diameter; and
  c) joining a plurality of the monofilaments to form a dental floss.

13. A method as in claim 12, wherein said abrasive particles are aluminum oxide.

14. A method as in claim 12, wherein said resin is nylon 612.

15. A method as in claim 12, wherein said abrasive particles have average size of 10 microns.

* * * * *